US012127979B2

United States Patent
Gliner et al.

(10) Patent No.: US 12,127,979 B2
(45) Date of Patent: Oct. 29, 2024

(54) ROBOTIC CATARACT SURGERY USING FOCUSED ULTRASOUND

(71) Applicant: JOHNSON & JOHNSON SURGICAL VISION, INC., Santa Ana, CA (US)

(72) Inventors: Vadim Gliner, Haifa (IL); Yoav Lamhot, Kiryat Bialik (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 619 days.

(21) Appl. No.: 17/022,577

(22) Filed: Sep. 16, 2020

(65) Prior Publication Data
US 2022/0079808 A1 Mar. 17, 2022

(51) Int. Cl.
*A61B 34/30* (2016.01)
*A61F 9/007* (2006.01)
(Continued)

(52) U.S. Cl.
CPC .......... *A61F 9/00745* (2013.01); *A61B 34/30* (2016.02); *A61B 2017/00057* (2013.01);
(Continued)

(58) Field of Classification Search
CPC ................. A61F 9/00745; A61B 34/30; A61B 2017/00057; A61B 2017/00084;
(Continued)

(56) References Cited

U.S. PATENT DOCUMENTS 3,805,787 A * 4/1974 Banko ..................... A61M 1/85 606/171
7,909,781 B2 3/2011 Schwartz
(Continued)

FOREIGN PATENT DOCUMENTS

KR 101574951 B1 * 12/2015
KR 101662775 B1 * 10/2016
(Continued)

OTHER PUBLICATIONS

Chen, K., Irie, T., Iijima, T et al. Double-parabolic-reflectors acoustic waveguides for high-power medical ultrasound. Sci Rep 9, 18493 (2019), pp. 1-10.
Miller et al., Overview of Therapeutic Ultrasound Applications and Safety Considerations., 2012 by the American Institute of Ultrasound in Medicine | J Ultrasound Med 2012; 31:623-634 | 0278-4297 | www.aium.org.
Brennen CE. 2015 Cavitation in medicine. Interface Focus 5: 20150022., http://dx.doi.org/10.1098/rsfs.2015.0022, pp. 1-12.

*Primary Examiner* — Brooke Labranche
*Assistant Examiner* — Nasheha Baset
(74) *Attorney, Agent, or Firm* — Johnson & Johnson Surgical Vision, Inc.

(57) ABSTRACT

A phacoemulsification apparatus includes an ultrasound transmitter, an irrigation-aspiration tool, a robotic arm, and a processor. The ultrasound transmitter is configured to generate and focus an ultrasound beam into a lens capsule of an eye of a patient, to emulsify a lens of the eye. The irrigation-aspiration tool having a distal end including an outlet of an irrigation channel for flowing irrigation fluid into the lens capsule, and an inlet of an aspiration channel for removing material from the lens capsule. The robotic arm is configured to move the distal end of the irrigation-aspiration tool inside the lens capsule. The processor is configured to control the ultrasound transmitter to irradiate one or more target locations in the eye capsule with the focused ultrasound beam, and control the robotic arm to move the distal end of the irrigation-aspiration tool in coordination with the target locations irradiated by the ultrasound transmitter.

8 Claims, 3 Drawing Sheets

(51) Int. Cl.
*A61B 17/00* (2006.01)
*A61B 17/32* (2006.01)
*A61B 34/20* (2016.01)
*A61N 7/00* (2006.01)
*A61N 7/02* (2006.01)

(52) U.S. Cl.
CPC .............. *A61B 2017/00084* (2013.01); *A61B 2017/32007* (2017.08); *A61B 2017/320084* (2013.01); *A61B 2034/2065* (2016.02); *A61B 2034/302* (2016.02); *A61B 2217/005* (2013.01); *A61B 2217/007* (2013.01); *A61N 2007/0069* (2013.01); *A61N 2007/0082* (2013.01); *A61N 7/02* (2013.01)

(58) Field of Classification Search
CPC ......... A61B 2017/32007; A61B 2017/320084; A61B 2034/2065; A61B 2034/302; A61B 34/25; A61B 2090/3937; A61B 2217/005; A61B 2217/007; A61B 2017/00106; A61B 2018/00648; A61B 2017/22014; A61B 2034/2063; A61B 2090/3966; A61N 2007/0069; A61N 7/02; A61N 2007/0056; A61N 7/00; A61N 2007/006; A61N 2007/0091; A61N 7/022; A61N 2007/0004; A61N 2007/0052
See application file for complete search history.

(56) References Cited

U.S. PATENT DOCUMENTS

| | | | |
|---|---|---|---|
| 8,102,734 | B2 | 1/2012 | Sliwa et al. |
| 9,403,039 | B2 | 8/2016 | Romano et al. |
| 2004/0082882 | A1 | 4/2004 | Rines |
| 2004/0152990 | A1 | 8/2004 | Mackool |
| 2011/0112400 | A1* | 5/2011 | Emery .................... A61N 7/00 601/3 |
| 2012/0253332 | A1* | 10/2012 | Moll .................... A61G 7/0503 606/4 |
| 2013/0103014 | A1* | 4/2013 | Gooding .............. A61B 3/0025 606/4 |
| 2014/0142591 | A1 | 5/2014 | Alvarez et al. |
| 2014/0194859 | A1* | 7/2014 | Ianchulev ........... A61F 9/00825 606/6 |
| 2014/0364870 | A1 | 12/2014 | Alvarez et al. |
| 2015/0018674 | A1* | 1/2015 | Scott ..................... A61B 3/107 600/407 |
| 2019/0105519 | A1* | 4/2019 | Herekar ................ A61B 8/463 |
| 2020/0289319 | A1* | 9/2020 | Carter ................ A61F 9/00736 |

FOREIGN PATENT DOCUMENTS

| | | | |
|---|---|---|---|
| RU | 2415640 C1 * | 4/2011 | |
| WO | 2010094353 A1 | 8/2010 | |
| WO | WO-2019197056 A1 * | 10/2019 | ......... A61B 17/3403 |

* cited by examiner

ROBOTIC CATARACT SURGERY USING FOCUSED ULTRASOUND

FIELD OF THE INVENTION

The present invention relates generally to robotic medical systems for eye surgery, and particularly to robotic phacoemulsification systems using focused ultrasound beam.

BACKGROUND OF THE INVENTION

A cataract is a clouding and hardening of the eye's natural lens, a structure which is positioned behind the 10 cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a 15 small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at 20 ultrasonic frequency to sculpt and emulsify the cataract while a pump aspirates particles and fluid from the eye through the tip. Alternatively, the surgeon may use a pulsed laser to break the cataracted lens into small pieces that can be aspirated. Either way, aspirated fluids are 25 replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule 30 restoring the patient's vision.

Various techniques to sculpt and emulsify a cataracted lens were proposed in the patent literature. For example, U.S. Pat. No. 9,403,039 describes a method of treating an ocular pathology by generating high intensity focused ultrasound onto at least one eye's area, the method comprises at least the following steps of: positioning onto the eye a device capable of directing high intensity focused ultrasound onto at least one annular segment, and generating high intensity focused ultrasound energy onto the segment to treat at least one annular segment in the eye. Another embodiment of the invention concerns a device for treatment of an ocular pathology comprising at least one eye ring wherein the proximal end of the eye ring is suitable to be applied onto the globe and a high intensity focused ultrasound beam generator to generate ultrasound beam fixed on the distal end of the eye ring capable of treating the whole circumference of the eye in one step.

As another example, U.S. Patent Application Publication 2019/0105519 describes methods and a system to provide a focused spot having a cross-sectional size within a range from about 50 um to about 200 um full width half maximum (FWHM); the corresponding cavitation can be similarly sized within similar ranges. The ultrasound beam can be focused and pulsed at each of a plurality of locations to provide a plurality of cavitation zones at each of the target regions. Each pulse may comprise a peak power within a range generating focal negative peak pressures within a range from about 10 MPa to about 80 MPa. While the treatment pulses can be arranged in many ways within a region, in many instances the pulses can be spaced apart within a region to provide intact tissue such as intact sclera between pulses.

U.S. Patent Application Publication 2004/0082882 describes a technique and apparatus for ameliorating, at least temporarily, vision-inhibiting effects of cataracts and the like within the lens of an eye. To this end, a MHz high-frequency ultrasound is used, having relatively low power, much less than that which would cause rupturing or fragmentation of the lens is used to treat the eye and for limited irradiation periods. The power is sufficient, however, to agitate and move around protein clumps or the like within the lens that cause the cataracts.

SUMMARY OF THE INVENTION

An embodiment of the present invention that is described hereinafter provides a phacoemulsification apparatus including an ultrasound transmitter, an irrigation-aspiration tool, a robotic arm, and a processor. The ultrasound transmitter is configured to generate and focus an ultrasound beam into a lens capsule of an eye of a patient, to emulsify a lens of the eye. The irrigation-aspiration tool, having a distal end including an outlet of an irrigation channel for flowing irrigation fluid into the lens capsule, and an inlet of an aspiration channel for removing material from the lens capsule. The robotic arm, which is configured to move the distal end of the irrigation-aspiration tool inside the lens capsule. The processor, configured to control the ultrasound transmitter to irradiate one or more target locations in the eye capsule with the focused ultrasound beam and control the robotic arm to move the distal end of the irrigation-aspiration tool in coordination with the target locations irradiated by the ultrasound transmitter.

In some embodiments, the processor is configured to control the robotic arm by registering a coordinate system of the robotic arm with a coordinate system of the ultrasound transmitter.

In some embodiments, the processor is further configured to control rates of irrigation and aspiration of the irrigation-aspiration tool, and transmission power of the ultrasound transmitter.

In an embodiment, the phacoemulsification apparatus further includes a thermal camera configured to acquire a thermal image of the lens capsule during emulsification of the lens, the thermal image being indicative of a temperature of the lens capsule.

In another embodiment, the ultrasound transmitter includes one of a paraboloid mirror and an ellipsoid mirror, for focusing the ultrasound beam.

In some embodiments, the processor is configured to control the ultrasound transmitter to irradiate the one or more target locations by moving the mirror so as to direct the focused ultrasound beam to the target locations.

In some embodiments, the processor is configured to move the mirror by at least one of tilting and translating the mirror.

In an embodiment, the robotic arm has at least three degrees of freedom.

In another embodiment, the phacoemulsification apparatus further includes a fluid filled tank, the tank having a shape conformal with the ultrasound transmitter and configured to establish a propagation path in the fluid for the ultrasound beam from the ultrasound transmitter to the eye.

The present invention will be more fully understood from the following detailed description of the embodiments thereof, taken together with the drawings in which:

Figure 1:
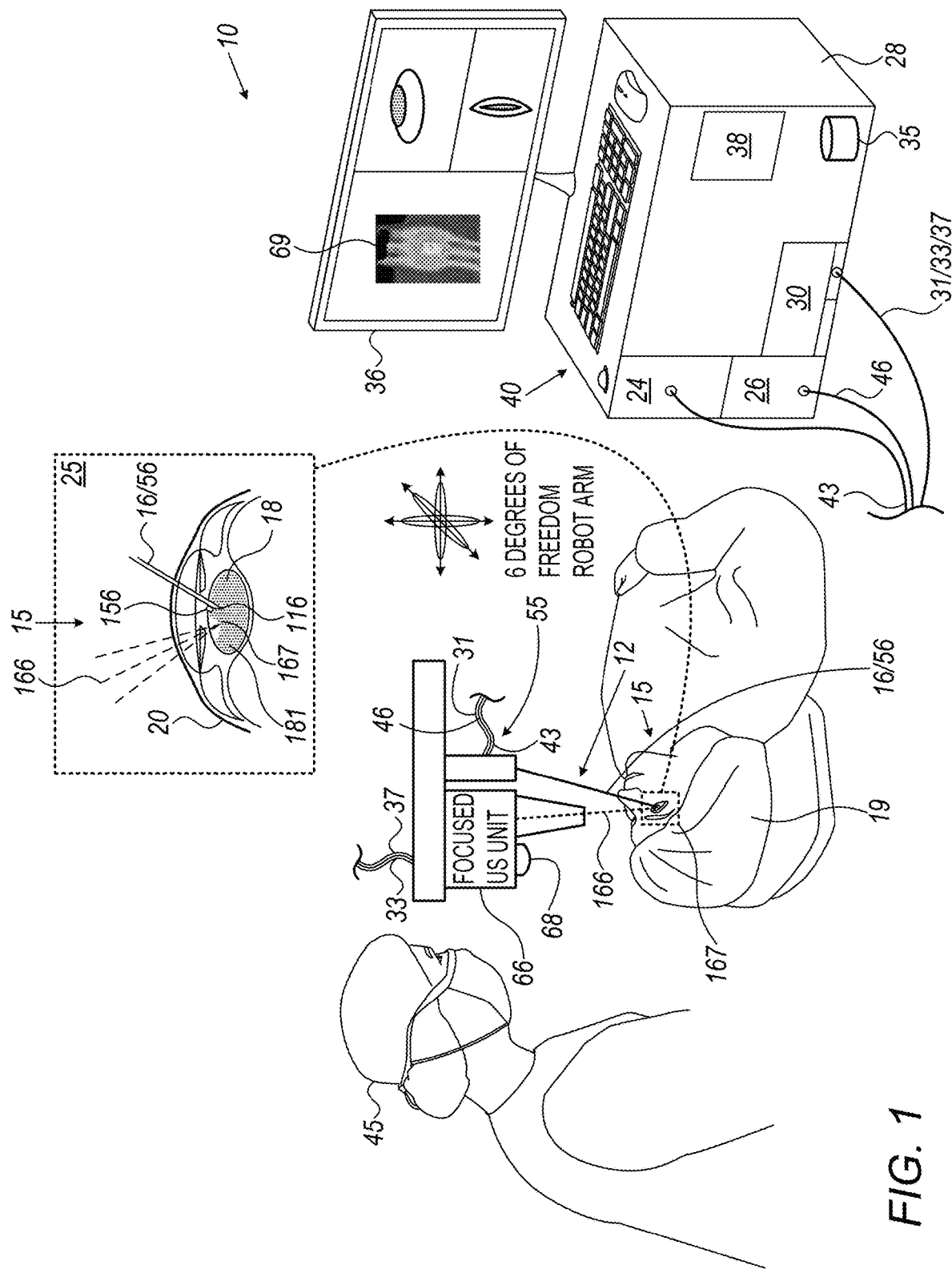
FIG. 1 is a schematic, pictorial view of a phacoemulsification apparatus comprising a focused ultrasound (US)
Figure 2:
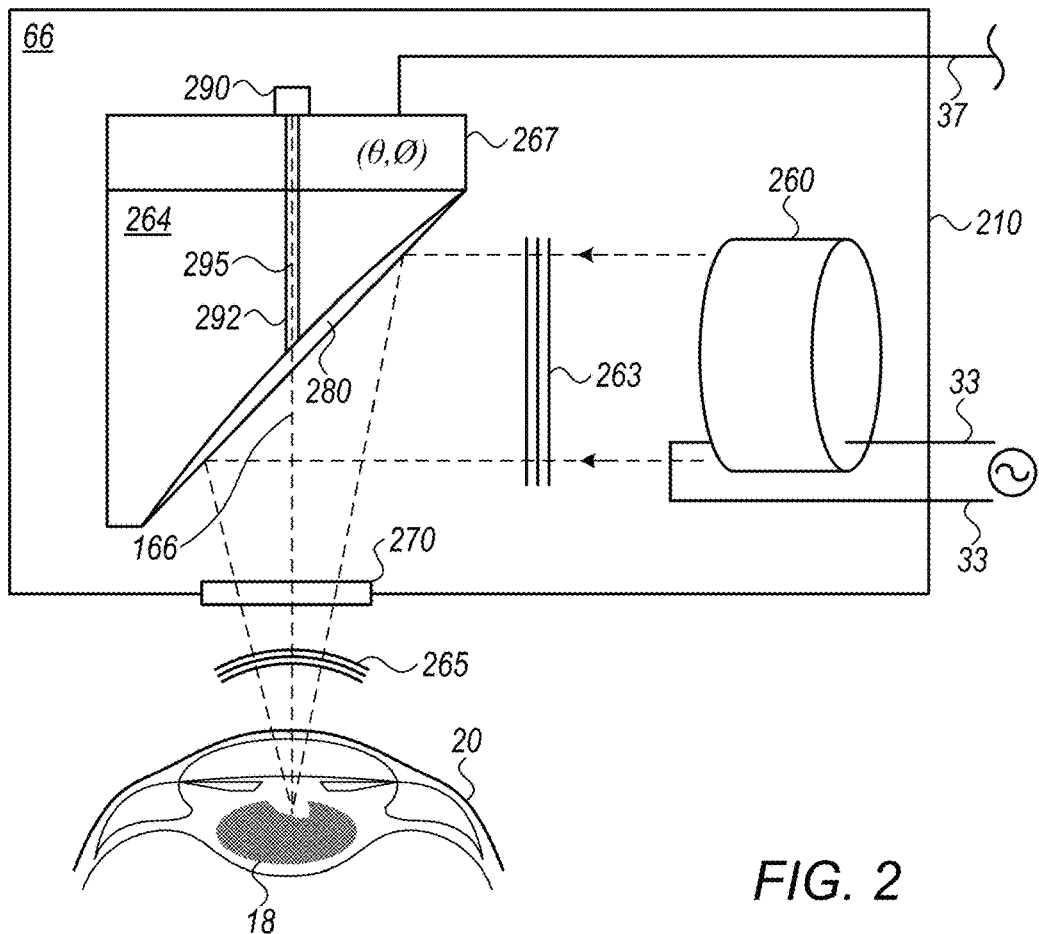
Figure 3:
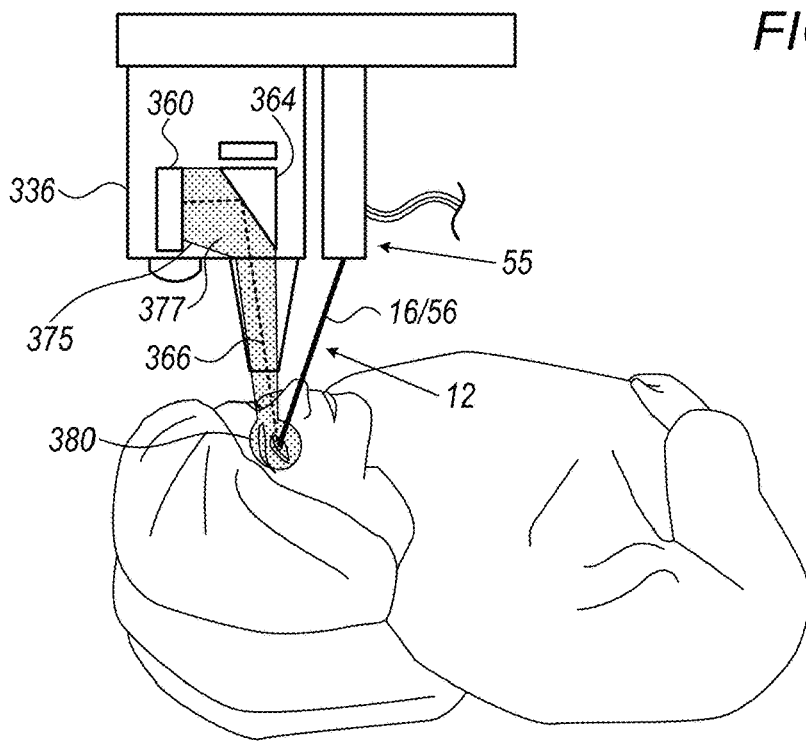
Figure 4:
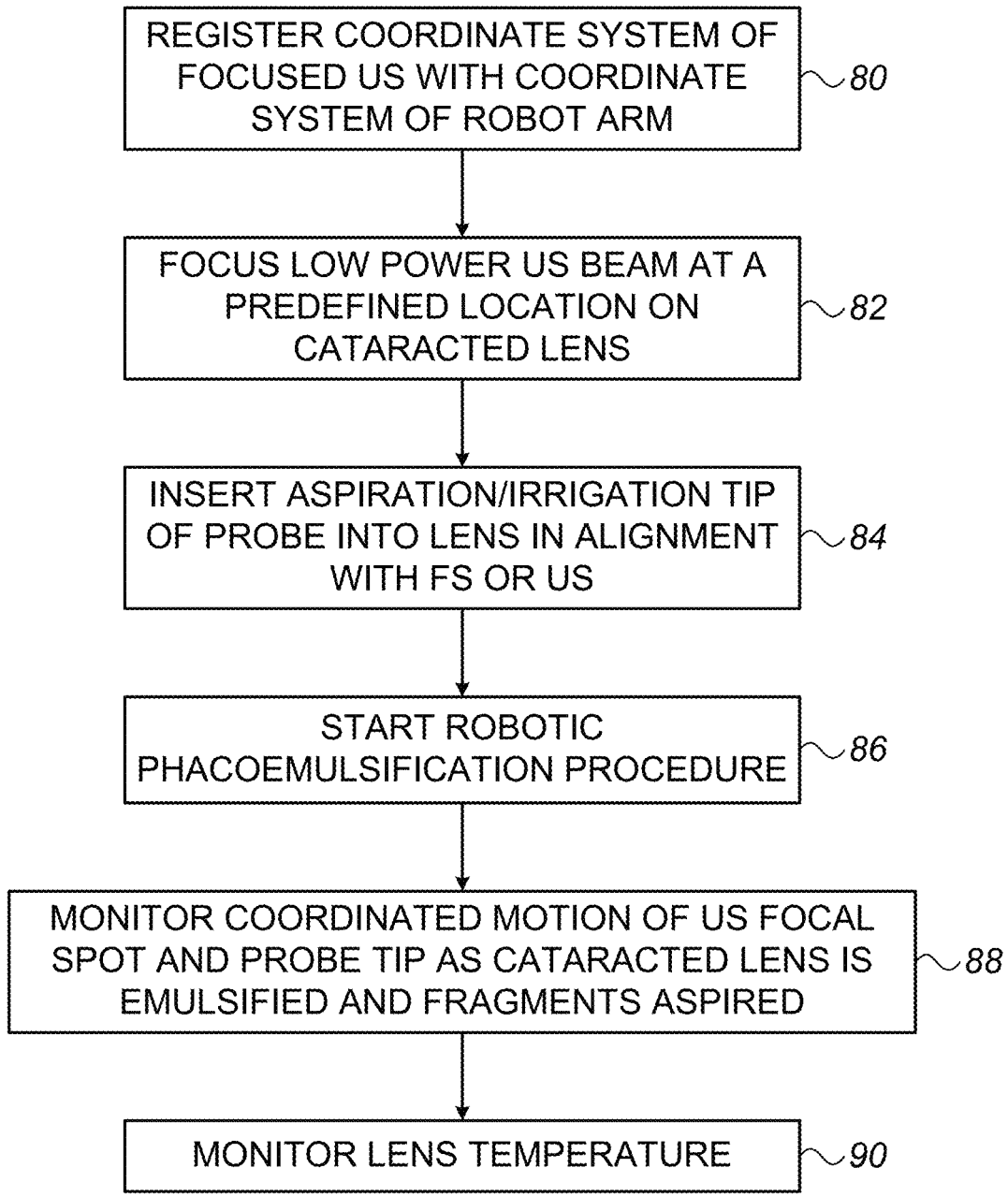

transmitter, and a robotic arm for coordinated aspiration/irrigation, in accordance with an embodiment of the present invention;

FIG. 2 is a block diagram schematically illustrating the focused ultrasound (US) transmitter of the apparatus of FIG. 1, in accordance with an embodiment of the present invention;

FIG. 3 is a block diagram schematically illustrating an ultra-high frequency focused ultrasound (US) transmitter, in accordance with another embodiment of the present invention; and FIG. 4 is a flow chart schematically illustrating a method for phacoemulsification using the apparatus of FIG. 1, in accordance with an embodiment of the present invention.

DETAILED DESCRIPTION OF EMBODIMENTS

Overview

Embodiments of the present invention that are described hereinafter provide methods and apparatuses that generate and focus a high frequency ultrasound (US) beam into a cataracted lens to induce cavitation, so as to emulsify the cataracted lens into particles. At the same time, using a robotic arm that follows the US beam at each location over the lens emulsified by the focused beam, the emulsified particles are aspirated, and replenishing of fluid is provided therein.

In some embodiments, a phacoemulsification apparatus is provided, which comprises an ultrasound transmitter, configured to generate and focus an ultrasound beam into the lens capsule of the eye of a patient, to emulsify a lens of the eye. The apparatus further comprises an irrigation-aspiration tool, having a distal end comprising an outlet of an irrigation channel for flowing irrigation fluid into the lens capsule, and an inlet of an aspiration channel for removing material from the lens capsule. A robotic arm of the apparatus is configured to move the distal end of the irrigation-aspiration tool inside the lens capsule. A processor of the apparatus is configured to (i) control the ultrasound transmitter to irradiate one or more target locations in the eye capsule with the focused ultrasound beam, and (ii) control the robotic arm to move the distal end of the irrigation-aspiration tool in coordination with the target locations irradiated by the ultrasound transmitter.

To this end, during the surgical procedure, a shaped mirror, such as a parabolic mirror, reflects and focuses an incident US beam, with the mirror variably tilting and/or translating according to commands from a processor, so that different target locations of the lens are cavitated and emulsified by the focused US beam. Particles produced by the focused US beam are aspirated via an inlet of an aspiration channel included in a rigid distal end of an aspiration/irrigation tool mounted on the robotic arm.

A processor-controlled (e.g., motorized) stage that moves the shaped mirror and the robotic arm are registered to the same coordinate system. This, and the accurate coordinated motion of the motorized stage and the robotic arm, allows the location of a tip of the rigid distal end of the aspiration/irrigation tool, where the aspiration inlet is located, to be maintained at or near the focused point of the ultrasound beam, as the latter moves during the surgical procedure. At the same time, an outlet of an irrigation channel included in the rigid distal end of the aspiration/irrigation tool enables the replenishment of fluid at each location.

The embodiments of the invention use a large area piezoelectric (PE) crystal, typically having a diameter of several centimeters, to generate an US wave of sufficient size and at a high enough frequency (e.g., >340 KHz), that can be focused to a sufficiently small focal spot (FS) (e.g., FS<1 mm) inside the lens capsule at the natural lens, using the paraboloid (or ellipsoid) mirror.

Above a certain US frequency, however, a US wave propagates poorly in air. To overcome this problem, in some embodiments, a conformal tank filled with fluid (e.g., saline solution) is comprised in a focused US transmitter. In this way, an ultra-high frequency US wave, generated and focused by the transmitter, propagates mostly though fluid media on its way to the eye, which can produce a very small FS with an ultra-high US frequency wave (e.g., >3.4 MHz, FS<0.1 mm).

In some embodiments, to ensure that eye temperature remains below a prespecified limit throughout the surgical procedure (e.g., <40° C.), the temperature of the eye is monitored with an infrared camera. The eye temperature is maintained below a specified limit by the processor that controls duration and amplitude of the applied ultrasound power based on a temperature feedback signal.

Using the disclosed emulsification apparatus, with its robotic and processor-controlled elements, allows for an accurate and less thermally hazardous cataract surgeries.

Apparatus Description

FIG. 1 is a schematic, pictorial view of a phacoemulsification apparatus 10 comprising a focused ultrasound (US) transmitter 66, and a robotic arm 55 for coordinated aspiration/irrigation, in accordance with an embodiment of the present invention.

As seen, focused US transmitter 66 directs a focused US beam (FS) 167 onto a lens 181 having a cataract in a lens capsule 18 of an eye 20 of a patient 19. Transmitter 66 comprises a processor-controlled tiltable and/or translatable paraboloid mirror (seen in FIG. 2), that allows apparatus 10 to vary a direction 166 and/or depth of FS along direction 166, according to a treatment plan under supervision of a physician 45.

As further seen, a rigid distal end 15 of an irrigation-aspiration tool 12 is coupled to robotic arm 55, the distal end comprising an aspiration channel 16 and an irrigation channel 56 (which can be coaxial or side-by-side). As inset 25 shows, aspiration channel 16 has an inlet 116, and irrigation channel 56 has an outlet 156, both at a distal tip of irrigation-aspiration tool 12, from which cataract fragments are aspirated and into which replenishing irrigation fluid flows, respectively. Rigid distal end 15 is shown straight, yet, it may be curved or bent. While the shown embodiment uses a robotic arm having six degrees of freedom, the number of degrees of freedom may vary with design, typically with a minimum of three (e.g., to point at a solid angle direction and vary depth).

Rigid distal end 15 is positioned such that aspiration inlet 116 and an irrigation outlet 156 are aligned in proximity of the focused US beam. During the phacoemulsification procedure, robotic arm 55 moves rigid distal end 15, so that aspiration inlet 116 and irrigation outlet 156 follow the FS location of the US beam, according to commands from a processor 38 communicated via a cable 31.

In the shown embodiment, console 28 comprises a piezoelectric drive module 30, which is coupled, using electrical wiring running in cable 33, with a piezoelectric crystal (seen in FIG. 2) inside transmitter 66, to generate the US beam. Drive module 30 is controlled by processor 38 to adjust a US power and/or duration and/or frequency. A processor-controlled stage inside transmitter 66, shown in FIG. 2, is configured to, at minimum, tilt direction 166 of FS 167 over lens capsule 18, according to a treatment plan that the processor executes by sending commands via a cable 37.

During the phacoemulsification procedure, a pumping sub-system 24 comprised in a console 28 pumps irrigation fluid from an irrigation reservoir to outlet 156 to irrigate the eye. In an embodiment, the irrigation fluid may be administered via a gravity fed method or any other known method in the art. The fluid is pumped via a tubing line 43 running from the console 28 to irrigation-aspiration tool 12. Eye fluid and waste matter (e.g., emulsified parts of the cataract) are aspirated via inlet 116 to the collection receptacle by a pumping sub-system 26 also comprised in console 28 and using a tubing line 46 running from irrigation-aspiration tool 12 to console 28.

In the shown embodiment, apparatus 10 further comprises a thermal camera 68 that captures a thermal image of lens capsule 18 in real time. The captured image 69 is displayed on a display 36. The displayed thermal image enables physician 45 to monitor and prevent thermal hazard to eye 20.

Processor 38 presents other results of the cataract removal procedure on display 36. Processor 38 may receive user-based commands via a user interface 40, which may include setting or adjusting an irrigation rate and/or aspiration rate. User interface 40 may be combined with a touch screen graphical user interface of display 36.

Some or all of the functions of processor 38 may be combined in a single physical component or, alternatively, implemented using multiple physical components. These physical components may comprise hard-wired or programmable devices, or a combination of the two. In some embodiments, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The apparatus shown in FIG. 1 may include further elements, which are omitted for clarity of presentation. For example, physician 45 may hold a control handle from which the physician can, for example, abort the automatic procedure. Physician 45 may use other surgical tools and/or apply medications, which are also not shown in order to maintain clarity and simplicity of presentation.

Focused US Transmitter for Phacoemulsification

FIG. 2 is a block diagram schematically illustrating focused ultrasound (US) transmitter 66 of apparatus 10 of FIG. 1, in accordance with an embodiment of the present invention. As seen, transmitter 66 comprises a large diameter piezoelectric transducer 260, where a typical diameter of transducer 260 ranges between 2 to 5 centimeters. Transducer 260 is driven by module 30 of FIG. 1 via a cable 33. The large size transducer generates an approximate planner US wave 263, which a paraboloid mirror 264 focuses (265) along direction 166, via an aperture 270 in a case 210 of transmitter 66.

A processor-controlled (via cable 37) tilting stage 267, is configured to tilt direction 166 of the FS over lens capsule 18, according to a treatment plan executed by the processor. Using a paraboloid surface 280 for mirror 260 removes spherical aberrations, and therefore may enable achieving a more compact focal spot.

In an embodiment, transmitter 66 further comprises a visible light laser marker/indicator (e.g., red laser) 290 coupled to the transmitter, that points at a direction 295 overlapping direction 166, at a location of the US focal spot 167 over lens capsule 18, to assist the physician. In the shown embodiment, the visible ray propagates inside a narrow (e.g., 1 mm in diameter) lumen 292 made to this end in stage 267 and mirror 264.

The example focused US transmitter shown in FIG. 2 is chosen purely for the sake of conceptual clarity. Such a transmitter may be constructed with alternative means to perform its functions, as would occur to a person skilled in the art. For example, a translation stage may be used instead of, or in addition to, stage 267, to move the FS over the lens and to change a depth (along direction 166) of the FS location inside lens capsule 18. Stage 267, or another stage (controlled by signals conveyed via cable 37), may include encoders to provide feedback to the processor on the movement. Alternatively, a sufficiently accurate mechanics may save the need for a full feedback scheme.

FIG. 3 is a block diagram schematically illustrating an ultra-high frequency focused ultrasound (US) transmitter 336, in accordance with another embodiment of the present invention. As seen, the US beam (366) that a transducer 360 generates and paraboloid mirror 364 focuses onto the eye, propagates almost a full path inside a conformal tank 375 filled with fluid 377. A suitable, typically soft contact end sleeve 380, enables bringing the fluid media closer to the eye, to further minimize US transmission losses in air. Soft end sleeve 380 can also accommodate motion of the rigid distal end of irrigation-aspiration tool 12.

The example focused US transmitter shown in FIG. 3 is chosen purely for the sake of conceptual clarity. In another example, the conformal tank may have an internal waterproof thermal camera to function as does camera 68 of FIG. 1.

FIG. 4 is a flow chart schematically illustrating a method for phacoemulsification using apparatus 10 of FIG. 1, in accordance with an embodiment of the present invention. The algorithm, according to the presented embodiment, carries out a process that begins with physician 45 operating apparatus 10 (e.g., processor 38) to register a coordinate system of focused US transmitter 66 with the coordinate system of robotic arm 55, at a coordinate system registration step 80. This step ensures that irrigation and aspiration are automatically and continuously applied at a current lens location at which the cataracted lens is emulsified.

Next, physician 45 operates transmitter 66 at low power to focus a low power US beam at a predefined location on the lens, at an US focal spot alignment step 82. As described in FIG. 2, in an embodiment, transmitter 66 further comprises visible light laser marker/indicator (e.g., red laser) 290 that points (in direction 295) at a location of the US focus over lens capsule 18, to assist the physician.

Next, physician 45 operates robotic arm 55 and thereby inserts the distal end 15 of irrigation-aspiration tool 12 into lens capsule 18 of an eye 20, in proximity to the FS of the US beam, at an irrigation-aspiration tool 12 tip insertion and alignment step 84.

At this point, physician 45 has apparatus 10 start the robotic phacoemulsification procedure by, for example, using a hand or foot control (not shown) to command processor 38 to start the procedure, at an automatic phacoemulsification step 86. During this step, processor 38 controls ultrasound transmitter 66 to irradiate one or more target locations in the eye capsule with the focused ultrasound beam, and controls robotic arm 55 to move distal end 15 of irrigation-aspiration tool 12 in coordination with the target locations irradiated by the ultrasound transmitter.

After the automatic phacoemulsification procedure commences, physician 45 monitors its progress by, for example, viewing parameters used in the procedure on display 36. Such parameters may include real time coordinates of the US FS and the distal end, actual US power and frequency, and the intraocular pressure (IOP), at a cataract removal procedure monitoring step 88.

In an embodiment, physician 45 further monitors a lens temperature to anticipate a thermal hazard, by, for example, viewing thermal image 69 on display 36, at an eye temperature monitoring step 90.

The example flow chart shown in FIG. 4 is chosen purely for the sake of conceptual clarity. For example, some of the manual monitoring steps can be performed by a processor, such as the IOP and temperature monitoring.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A phacoemulsification apparatus, comprising:
   an ultrasound transmitter, configured to generate and focus an ultrasound beam into a lens capsule of an eye of a patient, to emulsify a lens of the eye, wherein the ultrasound transmitter is located externally to the eye and the ultrasound beam is generated externally by the ultrasound transmitter and penetrates a cornea of the eye without contact of the ultrasound transmitter to the eye;
   an irrigation-aspiration tool, having a distal end comprising an outlet of an irrigation channel for flowing irrigation fluid into the lens capsule, and an inlet of an aspiration channel for removing material from the lens capsule;
   a fluid filled tank, the tank having a shape conformal with the ultrasound transmitter and configured to establish a propagation path in fluid for the ultrasound beam from the ultrasound transmitter to the eye and through which the irrigation-aspiration tool extends;
   a robotic arm, which is configured to move the distal end of the irrigation-aspiration tool inside the lens capsule; and a processor, configured to:
   control the ultrasound transmitter to irradiate one or more target locations in the eye capsule with the externally generated focused ultrasound beam; and
   control the robotic arm to move the distal end of the irrigation-aspiration tool in coordination with the target locations irradiated by the ultrasound transmitter.

2. The phacoemulsification apparatus according to claim 1, wherein the processor is configured to control the robotic arm by registering a coordinate system of the robotic arm with a coordinate system of the ultrasound transmitter.

3. The phacoemulsification apparatus according to claim 1, wherein the processor is further configured to control rates of irrigation and aspiration of the irrigation-aspiration tool, and transmission power of ultrasound transmitter.

4. The phacoemulsification apparatus according to claim 1, further comprising a thermal camera configured to acquire a thermal image of the lens capsule during emulsification of the lens, the thermal image being indicative of a temperature of the lens capsule.

5. The phacoemulsification apparatus according to claim 1, wherein the ultrasound transmitter comprises one of a paraboloid mirror and an ellipsoid mirror, for focusing the ultrasound beam.

6. The phacoemulsification apparatus according to claim 5, wherein the processor is configured to control the ultrasound transmitter to irradiate the one or more target locations by moving the mirror so as to direct the focused ultrasound beam to the target locations.

7. The phacoemulsification apparatus according to claim 6, wherein the processor is configured to move the mirror by at least one of tilting and translating the mirror.

8. The phacoemulsification apparatus according to claim 1, wherein the robotic arm has at least three degrees of freedom.

* * * * *